US012667534B2

(12) United States Patent
Olsson et al.

(10) Patent No.: US 12,667,534 B2
(45) Date of Patent: Jun. 30, 2026

(54) HIGH MOLECULAR WEIGHT ESTHETIC COMPOSITIONS

(71) Applicant: GALDERMA HOLDING SA, Zug (CH)

(72) Inventors: Johan Olsson, Bromma (SE); Morgan Karlsson, Almunge (SE)

(73) Assignee: Galderma Holding SA, Zug (CH)

( * ) Notice: Subject to any disclaimer, the term of this patent is extended or adjusted under 35 U.S.C. 154(b) by 247 days.

(21) Appl. No.: 18/348,736

(22) Filed: Jul. 7, 2023

(65) Prior Publication Data

US 2023/0346680 A1    Nov. 2, 2023

Related U.S. Application Data

(63) Continuation of application No. 17/108,729, filed on Dec. 1, 2020, now Pat. No. 11,730,691.

(60) Provisional application No. 62/942,624, filed on Dec. 2, 2019.

(51) Int. Cl.
| | |
|---|---|
| *A61K 8/04* | (2006.01) |
| *A61K 8/73* | (2006.01) |
| *A61Q 19/00* | (2006.01) |

(52) U.S. Cl.
CPC .............. *A61K 8/735* (2013.01); *A61K 8/042* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,332,812 A | 7/1994 | Nicolson et al. |
| 5,731,298 A | 3/1998 | Reinmuller |
| 6,132,750 A | 10/2000 | Perrier et al. |
| 6,495,314 B1 | 12/2002 | Kent et al. |
| 6,703,444 B2 | 3/2004 | Zhao et al. |
| 6,831,172 B1 | 12/2004 | Barbucci et al. |
| 7,731,758 B2 | 6/2010 | Asius et al. |
| 8,414,657 B2 | 4/2013 | Asius et al. |
| 8,858,999 B2 | 10/2014 | Giammona et al. |
| 8,887,243 B2 | 11/2014 | Thomson et al. |
| 10,105,197 B1 | 10/2018 | Colon |
| 10,889,894 B2 | 1/2021 | Hwung et al. |
| 11,198,765 B2 | 12/2021 | Olsson et al. |
| 11,254,792 B2 | 2/2022 | Olsson et al. |
| 11,530,301 B2 | 12/2022 | Mojarradi et al. |
| 11,643,509 B2 | 5/2023 | Mojarradi et al. |
| 11,708,461 B2 | 7/2023 | Olsson et al. |
| 2003/0093157 A1 | 5/2003 | Casares et al. |
| 2004/0014960 A1 | 1/2004 | Moon et al. |
| 2004/0072793 A1 | 4/2004 | Aeschlimann et al. |
| 2004/0197288 A1 | 10/2004 | Fleury et al. |
| 2004/0219630 A1 | 11/2004 | Tsubouchi |
| 2005/0025826 A1 | 2/2005 | Saikawa et al. |
| 2006/0166928 A1 | 7/2006 | Moon et al. |
| 2007/0053987 A1 | 3/2007 | Bayer et al. |
| 2007/0065481 A1 | 3/2007 | Chudzik et al. |
| 2007/0066816 A1 | 3/2007 | Tsai et al. |
| 2009/0011045 A1 | 1/2009 | Mertin et al. |
| 2009/0247741 A1 | 10/2009 | Zhao |
| 2010/0136070 A1 | 6/2010 | Dobak et al. |
| 2010/0255068 A1 | 10/2010 | Stroumpoulis et al. |
| 2010/0305175 A1 | 12/2010 | Krishnamoorthy et al. |
| 2010/0316683 A1 | 12/2010 | Piron et al. |
| 2012/0231046 A1 | 9/2012 | Asius et al. |
| 2013/0085187 A1 | 4/2013 | Kim et al. |
| 2013/0203697 A1 | 8/2013 | Hashimoto et al. |
| 2013/0338352 A1 | 12/2013 | Yasugi et al. |
| 2014/0094568 A1 | 4/2014 | James et al. |
| 2015/0045573 A1 | 2/2015 | Cheng et al. |
| 2016/0106718 A1 | 4/2016 | Gupta |
| 2018/0140530 A1 | 5/2018 | Bourdon et al. |
| 2019/0016830 A1 | 1/2019 | Olsson et al. |
| 2019/0023812 A1 | 1/2019 | Mojarradi et al. |
| 2019/0023855 A1 | 1/2019 | Olsson et al. |

FOREIGN PATENT DOCUMENTS

| | | |
|---|---|---|
| CN | 1529716 A | 9/2004 |
| CN | 1570128 A | 1/2005 |
| CN | 1694903 A | 11/2005 |
| CN | 101511876 A | 8/2009 |
| CN | 102952281 | 3/2013 |
| CN | 103038339 A | 4/2013 |

(Continued)

OTHER PUBLICATIONS

Jeon et al., "Mechanical properties and degradation behaviors of hyaluronic acid hydrogels cross-linked at various cross-linking densities", Apr. 12, 2007, Carbohydrate Polymers, vol. 70, pp. 251-257.
PubChem, "Hyaluronic Acid, MW 3,000", PubChem CID 155618327, accessed Apr. 30, 2025.
Borke et al., "Optimized triazine-mediated amidation for efficient and controlled functionalization of hyaluronic acid", Carbohydrate Polymers 116, Apr. 19, 2014, pp. 42-50.
Canova-Davis et al., "Chemical heterogeneity as a result of hydroxylamine cleavage of a fusion protein of human insulin-like growth factor I", Biochem. J., vol. 285, Jan. 6, 1992, pp. 207-213.
Crimmins et al., "Chemical Cleavage of Proteins in Solution", Current Protocols in Protein Science, 2005, pp. 11.4.1-11.4.11.
D'Este et al., "A systematic analysis of DMTMM vs EDC/NHS for ligation of amines to Hyaluronan in water", Carbohydrate Polymers 108, Mar. 14, 2014, pp. 239-246.

(Continued)

*Primary Examiner* — Brian Gulledge
(74) *Attorney, Agent, or Firm* — Sunit Talapatra; Foley & Lardner LLP

(57) ABSTRACT

Described are high molecular weight glycosaminoglycan (GAG) hydrogel compositions comprising GAGs covalently crosslinked with a carbohydrate crosslinker, and methods of making the high molecular weight GAG hydrogel compositions. Further described are methods of using the high molecular weight glycosaminoglycan (GAG) hydrogel compositions for reparative or plastic surgery, esthetic dermatology, facial contouring, body contouring, and gingival augmentation.

20 Claims, 5 Drawing Sheets

(56) References Cited

FOREIGN PATENT DOCUMENTS

| | | | |
|---|---|---|---|
| CN | 103788222 A | 5/2014 | |
| CN | 104194066 A | 12/2014 | |
| DE | 44 39 575 A1 | 5/1996 | |
| EP | 0 224 987 A2 | 6/1987 | |
| EP | 0 903 152 A2 | 3/1999 | |
| EP | 1 837 347 A1 | 9/2007 | |
| EP | 2 609 924 A1 | 7/2013 | |
| EP | 2 682 409 A1 | 1/2014 | |
| EP | 2 727 597 A1 | 5/2014 | |
| EP | 3 020 733 A1 | 5/2016 | |
| EP | 3 397 651 A1 | 11/2018 | |
| JP | S62-265998 A | 11/1987 | |
| JP | H11-152234 A | 6/1999 | |
| JP | 2002-519481 A | 7/2002 | |
| JP | 2004-507588 A | 3/2004 | |
| JP | 2004-511588 A | 4/2004 | |
| JP | 2006-505633 A | 2/2006 | |
| JP | 2009-507103 A | 2/2009 | |
| JP | 2014-531433 A | 11/2014 | |
| JP | 2015-537078 A | 12/2015 | |
| RU | 2230550 C2 | 6/2004 | |
| RU | 2434633 C2 | 11/2011 | |
| RU | 2448740 C2 | 4/2012 | |
| RU | 2653729 C2 | 5/2018 | |
| WO | WO-97/11958 A1 | 4/1997 | |
| WO | WO-00/01733 A1 | 1/2000 | |
| WO | WO-00/46252 A1 | 8/2000 | |
| WO | WO-00/46253 A1 | 8/2000 | |
| WO | WO-02/18450 A1 | 3/2002 | |
| WO | WO-02/30990 A1 | 4/2002 | |
| WO | WO-02/081739 A2 | 10/2002 | |
| WO | WO-02/082078 A2 | 10/2002 | |
| WO | WO-2004/011503 A1 | 2/2004 | |
| WO | WO-2004/057008 A1 | 7/2004 | |
| WO | WO-2007/026362 A2 | 3/2007 | |
| WO | WO-2008/008859 A2 | 1/2008 | |
| WO | WO-2013/086024 A2 | 6/2013 | |
| WO | WO-2014/064633 A1 | 5/2014 | |
| WO | WO-2014/072330 A1 | 5/2014 | |
| WO | WO-2015/021092 | 2/2015 | |
| WO | WO-2015/034436 | 3/2015 | |
| WO | WO-2015/043757 A1 | 4/2015 | |
| WO | WO-2015/181365 A1 | 12/2015 | |
| WO | WO-2015/181369 A1 | 12/2015 | |
| WO | WO-2017/114861 | 7/2017 | |
| WO | WO-2017/114864 A1 | 7/2017 | |
| WO | WO-2017/114865 | 7/2017 | |
| WO | WO-2017/114867 A1 | 7/2017 | |
| WO | WO-2019/002368 A1 | 1/2019 | |
| WO | WO-2019/002370 A1 | 1/2019 | |
| WO | WO-2019001784 A1 * | 1/2019 | ............. A61L 27/54 |

OTHER PUBLICATIONS

Gi Qisheng et al., "The Production and Clinical Application of Sodium Hyaluronate" Shanghai Science and Technology Press, 2012, pp. 1-6.

Gomez-Reyes et al., "Metal-catalyzed hydroxylaminolysis of unactivated amide and peptide bonds," Org. Biomol. Chem., vol. 1, Feb. 11, 2003, pp. 866-872.

Gupta et al., "Hydrogels for wound healing applications", Biomedical Hydrogels Biochemistry, 2011, pp. 184-227.

Hoffman, "Organic Chemistry, An Intermediate Text, Second Edition," John Wiley & Sons, Inc., 2004, p. 187 (4 pages).

International Search Report (PCT/ISA/210) issued on Jul. 31, 2017, by the European Patent Office as the International Searching Authority for International Application No. PCT/EP2017/063029 (5 pages).

International Search Report (PCT/ISA/210) mailed on Feb. 20, 2017, by the European Patent Office as the International Searching Authority for International Application No. PCT/EP2016/082778 (4 pages).

International Search Report (PCT/ISA/210) mailed on Feb. 20, 2017, by the European Patent Office as the International Searching Authority for International Application No. PCT/EP2016/082781 (4 pages).

International Search Report (PCT/ISA/210) mailed on Feb. 22, 2017, by the European Patent Office as the International Searching Authority for International Application No. PCT/EP2016/082783 (3 pages).

International Search Report (PCT/ISA/210) mailed on Feb. 23, 2017, by the European Patent Office as the International Searching Authority for International Application No. PCT/EP2016/082774 (5 pages).

International Search Report (PCT/ISA/210) mailed on May 10, 2017, by the European Patent Office as the International Searching Authority for International Application No. PCT/EP2016/082770 (5 pages).

International Search Report and Written Opinion on PCT Appl. Ser. No. PCT/IB2020/061336 dated Mar. 1, 2021 (9 pages).

International Search Report and Written Opinion on PCT PCT/IB2020/060066 dated Jan. 12, 2021 (14 pages).

Kurita et al., "Synthetic Carbohydrate Polymers Containing Trehalose Residues in the Main Chain: Preparation and Characteristic Properties," Macromolecules, vol. 27, No. 26, Jun. 27, 1994, pp. 7544-7549.

Lauder, "Chondroitin sulphate: A complex molecule with potential impacts on a wide range of biological systems", Complementary Therapies in Medicine, vol. 17, Nov. 26, 2008, pp. 56-62.

Maleki et al.; "Characterization of the chemical degradation of hyaluronic acid during chemical gelation in the presence of different cross-linker agents", Carbohydrate Research, vol. 342, Sep. 6, 2007, pp. 2776-2792.

Oladunni et al., "Chemically Modified N-Acylated Hyaluronan Fragments Modulate Proinflammatory Cytokine Production by Stimulated Human Macrophages," The Journal of Biological Chemistry, vol. 289, No. 36, Sep. 5, 2014. pp. 24779-24791.

Olson et al., "Specificity of Fatty Acid Acylation of Cellular Proteins," The Journal of Biological Chemistry, vol. 260, No. 6, Mar. 25, 1985, pp. 3784-3790.

Paterson et al., "Carbohydrate-Based Crosslinking Agents: Potential Use in Hydrogels", Journal of Polymer Science Part A: Polymer Chemistry, vol. 49, Aug. 17, 2011, pp. 4312-4315.

Rydergren, "Chemical Modifications of Hyaluronan using DMTMM-Activated Amidation, " Uppsala Universitet, Aug. 2013, pp. 1-30. (English Abstract only).

Schante et al., "Chemical modification of hyaluronic acid for the synthesis of derivatives for a broad range of biomedical applications", Carbohydrate Polymers 85, Mar. 21, 2011, pp. 469-489.

Shimizu et al., "Cleavage of unactivated amide bonds by ammonium salt-accelerated hydrazinolysis", ChemComm, 2014, pp. 12623-12625.

Shimizu et al., "Microwave-Assisted Deacylation of Unactivated Amides using Ammonium-Salt-Accelerated Transamidation", Angewandte Communications, vol. 51, 2012, pp. 8564-8567.

Stern et al., "The many ways to cleave hyaluronan", Biotechnology Advances, vol. 25, Jul. 18, 2007, pp. 537-557.

Tokita et al., "Hydrolytic degradation of hyaluronic acid", Polymer Degradation and Stability, vol. 48, 1995, pp. 269-273.

Tomihata et al., "Crosslinking of hyaluronic acid with water-soluble carbodiimide," Research Center for Biomedical Engineering, 1995-1996, pp. 243-251.

Tsigos et al., "Chitin deacetylases: new, versatile tools in biotechnology", Trends in Biotechnology, Elsevier Publications, Cambridge, vol. 18, No. 7, Jul. 1, 2000, XP004908536, pp. 305-312.

Werner et al., "Regulation of Wound Healing by Growth Factors and Cytokines", Physiol Rev, vol. 83, Jul. 2003, pp. 835-870.

Written Opinion (PCT/ISA/210) issued on Jul. 31, 2017 by the European Patent Office as the International Searching Authority for International Application No. PCT/EP2017/063029 (6 pages).

Written Opinion (PCT/ISA/237) mailed on Feb. 20, 2017, by the European Patent Office as the International Searching Authority for International Application No. PCT/EP2016/082778 (5 pages).

Written Opinion (PCT/ISA/237) mailed on Feb. 20, 2017, by the European Patent Office as the International Searching Authority for International Application No. PCT/EP2016/082781 (6 pages).

(56) References Cited

OTHER PUBLICATIONS

Written Opinion (PCT/ISA/237) mailed on Feb. 22, 2017, by the European Patent Office as the International Searching Authority for International Application No. PCT/EP2016/082783 (4 pages).

Written Opinion (PCT/ISA/237) mailed on Feb. 23, 2017, by the European Patent Office as the International Searching Authority for International Application No. PCT/EP2016/082774 (7 pages).

Written Opinion (PCT/ISA/237) mailed on May 10, 2017, by the European Patent Office as the International Searching Authority for International Application No. PCT/EP2016/082770 (6 pages).

Zhu et al., "Selective cleavage of isoaspartyl peptide bonds by hydroxylamine after methyltransferase priming", Analytical Biochemistry, Elsevier, Amsterdam, NL, vol. 364, No. 1, Mar. 31, 2007, XP022005959, pp. 1-7.

Ahmed, E., "Hydrogel: Preparation, characterization, and applications: A review", Journal of Advanced Research, vol. 6, 2015, pp. 105-121.

* cited by examiner

HIGH MOLECULAR WEIGHT ESTHETIC COMPOSITIONS

CROSS-REFERENCE TO RELATED APPLICATIONS

This application is a continuation of U.S. application Ser. No. 17/108,729, filed Dec. 1, 2020, which claims the benefit of priority to U.S. application Ser. No. 62/942,624, filed Dec. 2, 2019, which are herein incorporated by reference in their entireties.

FIELD

The present disclosure relates to the field of high molecular weight esthetic compositions such as hydrogels containing crosslinked polysaccharides, and the use of such hydrogels in medical and/or cosmetic applications such as implants for subcutaneous or intradermal injection, which may be used in humans in reparative or plastic surgery and in esthetic dermatology. More specifically, the present disclosure is concerned with hydrogels comprising crosslinked high molecular weight glycosaminoglycans (GAGs), particularly crosslinked hyaluronic acid, chondroitin, or chondroitin sulfate.

BACKGROUND

Hydrogels are widely used in medicine—prepared by chemical crosslinking polymers to form large polymeric networks. While both monomeric and minimally polymerized polysaccharides both absorb water to the point of saturation, polysaccharides dissolve at the point of saturation while hydrogels comprising the same polysaccharides, albeit crosslinked, can typically absorb water without dissolving, resulting in a swelling of the hydrogel.

All glycosaminoglycans (GAGs) are negatively charged long linear heteropolysaccharides that have a capacity to absorb large amounts of water. Hyaluronic acid, chondroitin, and chondroitin sulfate are well-known biocompatible GAGs utilized in medical and cosmetic applications. One of the most widely used biocompatible polymers for medical use is hyaluronic acid, and derivatives thereof. Modifying hyaluronic acid molecules through crosslinking and other means is necessary to improve the duration of hyaluronic acid in vivo, such as crosslinking hyaluronic acid to form a hyaluronic acid hydrogel.

Producing hydrogels from high molecular weight GAGs, such as hyaluronic acid results in a suitable filler for multiple types of medical or cosmetic applications; however, the hydrogel may degrade or hydrolyze during storage or during degrading conditions such as heat sterilization or accelerated stability studies. Methods of increasing the stability of the hydrogels include increasing the number of crosslinks in the hydrogels, but increasing the number of crosslinks of high molecular weight GAGs can produce hydrogels that are stable under degrading conditions but results in a phase separation of the hydrogel. This presents problems to then diluting hydrogels without obtaining phase separation.

The aim of the present disclosure is to overcome the problems associated with preparing hydrogels from high molecular weight GAGs that exhibit increased stability and are able to maintain the integrity of the hydrogel during degradation conditions, such as heat sterilization, while maintaining the ability to dilute hydrogels to desired GAG concentrations for applications such as filling syringes with hydrogels.

SUMMARY OF THE DISCLOSURE

The present disclosure is generally drawn to methods of producing a hydrogel from crosslinked high molecular weight glycosaminoglycans (GAGs) capable of maintaining the structural integrity under conditions that would otherwise hydrolyze the hydrogel or result in a phase separation of the hydrogel. The present disclosure is further drawn to hydrogel compositions produced by the methods.

In some aspects, the disclosure is generally drawn to a method of preparing a hydrogel comprising crosslinked glycosaminoglycan (GAG) molecules, said method comprising (a) crosslinking a GAG having a molecular weight of at least 1.5 MDa with a crosslinker, wherein the concentration of GAG is between 2% to 10% (w/w) and the molar ratio of the crosslinker to GAG is less than or equal to 2%, to obtain a glycosaminoglycan hydrogel crosslinked by amide bonds.

In some aspects, if the GAG concentration in (a) is between 1% to 4.5% (w/w), then the concentration of crosslinker is between 0.8 to 2 mol % per GAG disaccharide; and if the GAG concentration in (a) is between 4.6% to 5.9% (w/w), then the concentration of crosslinker is between 0.5 to 0.8 mol % per GAG disaccharide; and if the GAG concentration in (a) is between 6% to 12% (w/w), then the concentration of crosslinker is between 0.3 to 0.5 mol % per GAG disaccharide.

In some aspects, the crosslinker in (a) is a di- or multi-nucleophile functional crosslinker. In some aspects, the di- or multinucleophile functional crosslinker is an aliphatic or aromatic diamino derivative, a peptide or a peptide sequence. In some aspects, the di- or multinucleophile functional crosslinker comprises a spacer group selected from the group consisting of di-, tri-, tetra-, and oligosaccharides. In some aspects, the di- or multinucleophile functional crosslinker is diaminotrehalose (DATH).

In some aspects, the crosslinking of (a) comprises: a1) providing or obtaining a solution of glycosaminoglycan (GAG) molecules; a2) activating carboxyl groups on the glycosaminoglycan molecules with a coupling agent to form activated glycosaminoglycan molecules; and a3) crosslinking the activated glycosaminoglycan (GAG) molecules via their activated carboxyl groups using a di- or multinucleophile functional crosslinker to obtain a glycosaminoglycan hydrogel crosslinked by amide bonds. In some aspects, the coupling agent used in a2) is a triazine-based coupling agent, such as 4-(4,6-dimethoxy-1,3,5-triazin-2-yl)-4-methylmorpholinium chloride (DMTMM).

In some aspects, the crosslinking in (a) is performed at a pH of 5.0-9.0, preferably at a pH of 6.0-8.0. In some aspects, the methods further comprise the formulating the crosslinked hydrogel obtained from (a) to a final glycosaminoglycan (GAG) concentration of 10-30 mg/mL. In some aspects, the methods further comprise (b) sterilizing the crosslinked hydrogel obtained from (a).

In some aspects, the glycosaminoglycan (GAG) is hyaluronic acid (HA). In some aspects, the GAG in (a) has a molecular weight of 2.0-10 MDa, preferably 2.5-3.5 MDa. In some aspects, the concentration of GAG is between 3-5% (w/w). In some aspects, the molar ratio of crosslinker to GAG is between 0.9-1.1%. In some aspects, the GAG is hyaluronic acid (HA) having a molecular weight of 2.5-3.5 MDa and the crosslinker is diaminotrehalose (DATH), and further wherein the concentration of HA is between 3-5% (w/w) and the molar ratio of DATH to HA is between 0.9-1.1%.

In some aspects, the disclosure is generally drawn to a hydrogel product obtained by any one of the methods described herein. In some aspects, the disclosure is generally drawn to a hydrogel product comprising glycosaminoglycan (GAG) molecules as the swellable polymer, wherein the glycosaminoglycan molecules are crosslinked by amide bonds and wherein the apparent molecular weight (Mwapp) of the crosslinked glycosaminoglycan molecules is above 1.0 MDa; and wherein the thermostability of the swellable polymer (NormGelC) is above 80% after 24 hours.

In some aspects, the glycosaminoglycan molecules are covalently crosslinked via crosslinks comprising a spacer group selected from the group consisting of di-, tri-, tetra-, and oligosaccharides. In some aspects, the spacer group is trehalose. In some aspects, the glycosaminoglycan (GAG) is hyaluronic acid (HA). In some aspects, the hydrogel product is sterilized.

According to any one or more of the previous aspects, the GAG does not have a molecular weight of less than 1.5 MDa, or optionally, less than 1.4 MDa, 1.3 MDa, 1.2 MDa, 1.1 MDa, 1.0 MDa, 0.9 MDa, 0.8 MDa, or 0.7 MDa.

According to any one or more of the above aspects, the hydrogel is not subjected to a post-crosslinking degradation of the glycosaminoglycan. According to any one or more of the above aspects, the hydrogel is subject to ambient degradation post-crosslinking; however, the hydrogel does not exhibit a $C_{min}$ value below that of $C_{final}/2$. According to any one or more of the above aspects, the hydrogel exhibits a $C_{min}$ value greater than $C_{final}/2$ of the hydrogel.

In some aspects, the (a) and (b) are performed stepwise from (a) to (b). In some aspects, a1), a2), and a3) are performed stepwise from a1) to a2) to a3). In some aspects, (a) and (b) are not performed stepwise from (a) to (b). In some aspects, a1), a2), and a3) are not performed stepwise from a1) to a2) to a3).

In some aspects, the disclosure is generally drawn to a method of cosmetically treating skin, which comprises administering to the skin a hydrogel product according to any one of the hydrogel compositions described herein.

The following detailed description is exemplary and explanatory, and is intended to provide further explanation of the invention.

DETAILED DESCRIPTION OF THE DISCLOSURE

I. Definitions

Figure 1:
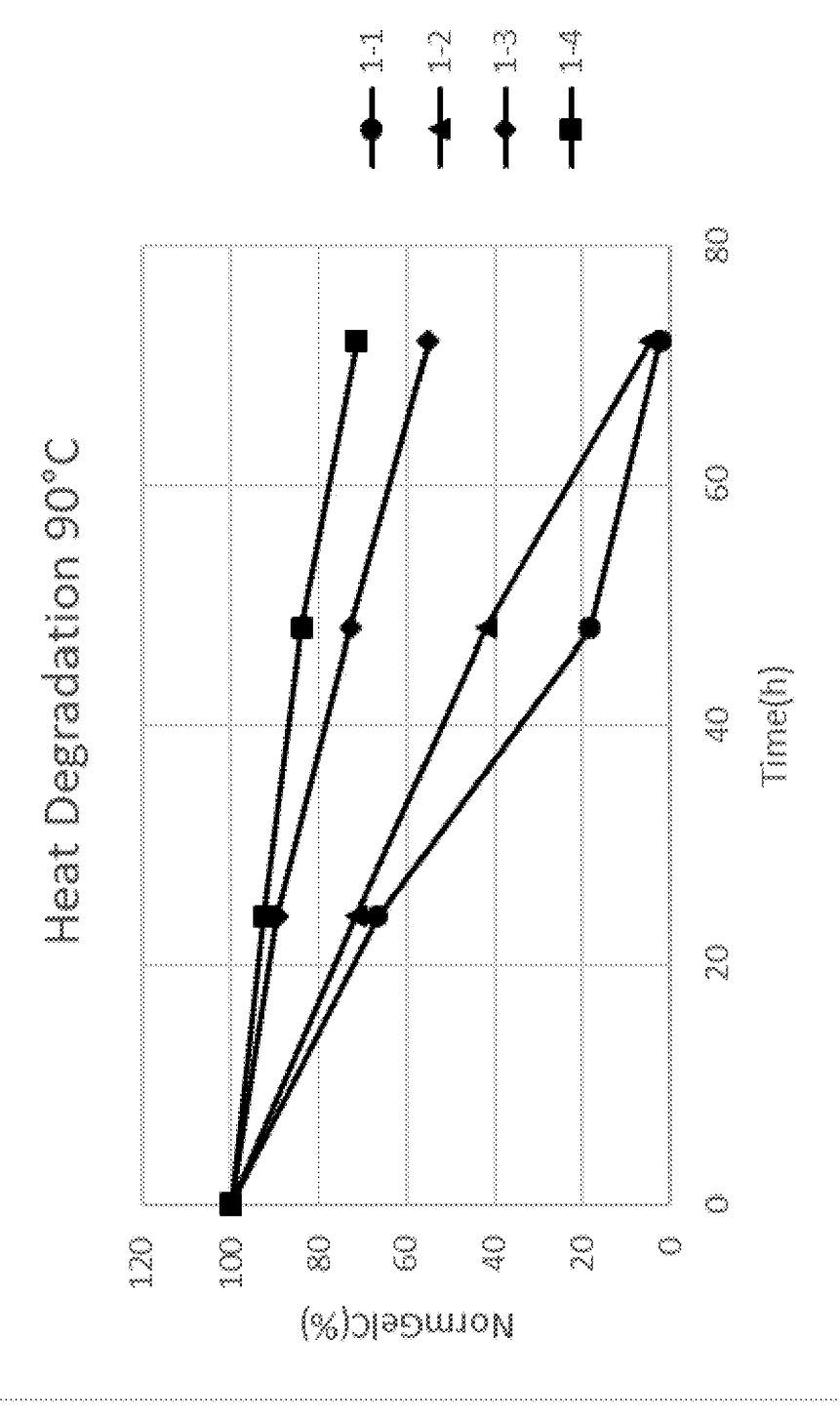
FIG. 1 depicts the normalized gel content (NormGelC (%)) for four gel samples that exhibit various HA (MW) and HA crosslinking over a period of approximately 70 hours at 90° C.

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, the terms "about" or "approximately" when preceding a numerical value indicates the value plus or minus a range of 10% of the value.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, a "control" is an alternative sample used in an experiment for comparison purpose. A control can be "positive" or "negative." A "control sample" or "reference sample" as used herein, refers to a sample or reference that acts as a control for comparison to an experimental sample. For example, an experimental sample comprises compound A, B, and C in a vial, and the control may be the same type of sample treated identically to the experimental sample, but lacking one or more of compounds A, B, or C.

As used herein, the term "effective amount" refers to a quantity sufficient to achieve a desired therapeutic and/or prophylactic effect, e.g., an amount which results in the prevention of one or more outcomes, or an increase in one more outcomes.

As used herein, the terms "individual", "patient", or "subject" can be an individual organism, a vertebrate, a mammal, or a human. In a preferred aspect, the individual, patient, or subject is a human.

As used herein, the phrase "soft tissue" refers to tissues that connect, support, or surround other structures and organs of the body. Soft tissue includes muscles, fibrous tissues, and fat.

As used herein, the phrase "soft tissue augmentation" refers to any type of volume augmentation of soft tissues, including, but not limited to facial contouring (e.g., more pronounced cheeks, chin, or lips), correction of concave deformities (e.g., post-traumatic or HIV-associated lipoatrophy), and correction of deep age-related facial folds. Thus, soft tissue augmentation may be used for cosmetic purposes or for medical purposes, such as those following trauma or degenerative disease. Soft tissue augmentation further refers to dermal filling, body contouring, and gingival filling.

As used herein, the phrase "non-animal origin" refers to a source that excludes animals, but includes sources such as yeast, bacteria, or synthetic.

As used herein, the term "bioresorbable" refers to a degradation event or events—bioresorbable substances may dissolve, may be phagocytized, or may simply degrade over a period of time such that the substances are cleared from the body, organ, tissue, location, or cell over a period of time. The substances or degradation products thereof may be metabolized, incorporated into other molecules or compounds, or excreted.

As used herein, the term "aseptic" refers to something that is free or freed from pathogenic microorganisms.

As used herein, the term "sterile" refers to something that is free of living organisms, generally free of living microorganisms.

As used herein, the term "injectable" refers to the ability to inject a composition of the present disclosure through a needle.

As used herein, the terms "MW" or "Mw" refer to the mass average molecular mass.

As used herein, the term "MW$_{app}$" refers to apparent MW, which is a simulated value for the molecular weight of GAGs in hydrogels.

As used herein, the term "SwF" refers to the swelling factor analysis in saline, which is the volume of saline for a 1 gram gel that has swelled to its maximum—usually represented in mL/g).

As used herein, "gel content" or "GelC" refer to the percentage in the proportion of the total HA that is bound in gel form—further described as the amount of HA in a sample that does not pass through a 0.22 micrometer filter. The GelC is calculated from the amount of HA that is collected in the filtrate and is reported as the percentage of the total amount of HA in the gel sample.

As used herein, "SwD" refers to the swelling degree, which is the inverted concentration of gel-form GAG in a gel that is fully swollen in 0.9% saline, i.e., the volume or mass of a fully swollen gel that can be formed per gram of dry crosslinked GAG. The SwD generally describes the maximal liquid-absorbing (0.9% saline) capability of the product. SwD is preferably expressed in g/g, mL/g, or as a dimensionless number.

$$SwD = \frac{mass\,(fully\,swollen\,gel)}{mass\,(gel\text{-}form\,GAG\,in\,fully\,swollen\,gel)}$$

The SwD may also be expressed as $$SwD = \frac{[GAG] * GelC}{SwF}$$

As used herein, "CrR$_{DATH}$" refers to the effective cross-linking ratio that was analyzed with LC-SEC-MS, more specifically defined as $$CrR = \frac{mol\,crosslinked\,crosslinker\,with\,amide\,bonds}{mol\,linked\,crosslinker\,with\,amide\,bonds}$$

A CrR of 1.0 indicates that all of the crosslinker has crosslinked.

As used herein, "C$_{min}$" is the minimum theoretical GAG concentration—the concentration of gel-form GAGs in a gel that is fully swollen in 0.9% saline, typically expressed in mg/g or mg/mL.

The $C_{min}^{-1}$=SwD

As used herein, "C$_{final}$" is the intended concentration of the GAG in the final hydrogel product. In some aspects, C$_{final}$ is greater than 2×C$_{min}$.

The present technology is not to be limited in terms of the particular aspects described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

II. Hydrogels and Methods of Making Hydrogels

Fillers such as dermal fillers have been used to repair, restore or augment hard or soft tissue contour defects of the body due to aging, injury, or acquired or congenital deformities of the face, body and internal organs. Fillers may be natural or synthetic substances that are used to reduce wrinkles and/or fine lines, restore lost volume, hydrate the skin, soften nasolabial folds, augment and contour lips, improve scars (depressed, hypertrophic and keloid scars), strengthen weakened vocal cords, and provide other soft tissue improvements. Substances that have been utilized include fat, paraffin, human collagen, bovine collagen, silicone, hyaluronic acids, lactic acids, and glycolic acids. In 1981, a new era in soft tissue fillers emerged with the FDA approval of bovine collagen. Since then, many soft tissue fillers have emerged. The dramatic increase in the number of current and investigational fillers has been fueled by many factors including improvements in biotechnology and an emphasis on cosmetic appearance in society. With the introduction of newer fillers, there has been an ongoing need to evaluate their risk/benefit profiles and define their limitations in order to maximize patient cosmetic outcomes and safety. Common filler/hydrogel compositions include GAGs such as hyaluronic acid.

Methods of producing GAG hydrogels are disclosed in PCT publication numbers WO2017/114867, WO2017/114861, WO2017/114864, and WO2017/114865; US Pregrant Publication Numbers US20190023812A1, US20190016830A1, US20190023855A1, and US20070066816A1; and U.S. Pat. Nos. 8,858,999, 6,831,172, 8,887,243, and, 6,703,444.

A common route for crosslinking hyaluronic acid is using a diglycidyl ether, e.g. 1,4-butanediol diglycidyl ether (BDDE). As an alternative, amide coupling using a di- or multiamine functional crosslinker together with a coupling agent is an attractive route for preparing crosslinked hyaluronic acid molecules useful for hydrogel products. For example, the use of 4-(4,6-Dimethoxy-1,3,5-triazin-2-yl)-4-methylmorpholinium chloride (DMTMM) for activation of carboxylate and subsequent condensation with a diamino structure, e.g. diaminotrehalose (DATH) has shown to be an efficient method to produce hydrogels composed of crosslinked hyaluronic acid with minor degradation of the biopolymer.

In some aspects, crosslinking is performed via crosslinkers comprising a spacer group selected from the group consisting of di-, tri-, tetra-, and oligosaccharides. This provides a hydrogel product based entirely on carbohydrate structures or derivatives thereof, which minimizes the disturbance of the crosslinking on the native properties of the GAGs utilized in producing the hydrogel.

In some aspects, the crosslinker itself contributes to maintained or increased properties of the hydrogel, for example when crosslinking with a structure that correlates to hyaluronic acid (e.g., diamino hyaluronic acid tetrasaccharide) or when crosslinking with a structure with high water retention properties (e.g., trehalose).

In some aspects, the GAG is a sulfated or non-sulfated GAG such as hyaluronan, chondroitin sulphate, heparan sulphate, heparosan, heparin, dermatan sulphate and keratan sulphate. In some aspects, the GAG is hyaluronic acid, chondroitin or chondroitin sulfate. In one aspect, the GAG is hyaluronic acid. In some aspects, the GAG is a native GAG. In some aspects, the GAG is a naturally occurring GAG. In some aspects, the GAG is used in its native state (i.e., the chemical structure of the GAG has not been altered or modified by addition of functional groups or the like). Using the GAG in its native state is preferred because this will afford a crosslinked structure more closely resembling the natural molecules, which conserves the native properties and effects of the GAG itself, and can minimize the immune response when the crosslinked GAG is introduced into the body.

In some aspects, the GAGs are covalently crosslinked. In some aspects, the covalently crosslinked GAG molecules consist of, or essentially consist of carbohydrate type structures or derivatives thereof. In some aspects, the crosslinked GAGs or hydrogels are free of, or essentially free of synthetic non-carbohydrate structures or linkers. This can be achieved by using a GAG in its native state together with a crosslinker which comprises, consists of, or essentially consist of carbohydrate type structures or derivatives thereof. In some aspects, functional groups of the crosslinker are covalently bound directly to carboxyl groups of the GAG. In some aspects, the crosslinks of the covalently crosslinked GAGs comprise, consist of, or essentially consist of di-, tri-, tetra-, and oligosaccharide spacer groups.

In some aspects, the crosslinked GAG comprises crosslinks between the GAG molecule chains, which creates a continuous network of GAG molecules held together by covalent crosslinks.

In some aspects, the crosslinked GAGs form a gel or hydrogel—water-insoluble, but substantially dilute crosslinked system of GAGs when subject to liquid, typically an aqueous liquid.

In some aspects, the process of preparing a hydrogel product comprising crosslinked glycosaminoglycan molecules, comprises, consists of, or consists essentially of: (a) providing a solution of glycosaminoglycan molecules; (b) activating carboxyl groups on the glycosaminoglycan molecules with a coupling agent to form activated, glycosaminoglycan molecules; and (c) crosslinking the activated glycosaminoglycan molecules via their activated carboxyl groups using a di- or multinucleophile functional crosslinker comprising a spacer group selected from the group consisting of di-, tri-, tetra-, and oligosaccharides to obtain crosslinked glycosaminoglycan molecules.

In some aspects, the GAGs are crosslinked by covalent bonds, such as amide bonds, typically using an activating agent for the carboxyl groups on the GAG molecule backbone and a di- or multinucleophile functional crosslinker comprising a spacer group selected from the group consisting of di-, tri-, tetra-, and oligosaccharides. In some aspects, crosslinking of the GAGs can be achieved by mild and efficient routes resulting in high yields with minimal degradation of the GAG molecules.

In some aspects, the di- or multinucleophile functional crosslinker contains a spacer group selected from the group consisting of di-, tri-, tetra-, and oligosaccharides, which remains in the crosslinks between the GAG molecules. In some aspects, the di- or multinucleophile functional di-, tri-, tetra-, and oligo-saccharides comprise at least two nucleophile functional groups attached thereto. In some aspects, the at least two nucleophile functional groups are separated by the spacer group selected from the group consisting of di-, tri-, tetra-, and oligosaccharides.

In some aspects, the di- or multinucleophile functional crosslinker comprises two or more functional groups capable of reacting with functional carboxyl groups of the GAG, resulting in the formation of covalent bonds, such as amide bonds. In some aspects, the nucleophile functional groups are capable of reacting with carboxyl groups on the glycosaminoglycan molecule to form amide bonds. In some aspects, the nucleophile functional groups of the di-, tri-, tetra-, and oligosaccharides are selected from the group consisting of primary amine, hydrazine, hydrazide, carbazate, semi-carbazide, thiosemicarbazide, thiocarbazate and aminoxy. In some aspects, the di- or multinucleophile functional di-, tri-, tetra-, and oligo-saccharides may be derived from nucleophile functional polysaccharides, such as chitobiose derived from chitin. In some aspects, the di- or multinucleophile functional di-, tri-, tetra-, and oligo-saccharides may also be di-, tri-, tetra-, and oligo-saccharides which have been modified by introduction of two or more nucleophile functional groups.

In some aspects, the di- or multinucleophile functional crosslinker include homo- or heterobifunctional primary amines, hydrazines, hydrazides, carbazates, semi-carbazides, thiosemicarbazides, thiocarbazates and aminoxy.

In some aspects, the crosslinker is selected from the group consisting of diamino hyaluronic acid tetrasaccharide, diamino hyaluronic acid hexasaccharide, diamino trehalose (DATH), diamino lactose, diamino maltose, diamino sucrose, diamino chitobiose, chitobiose, or diamino raffinose.

In some aspects, the activation step and the crosslinking step occur simultaneously. In some aspects, the activation step occurs prior to and separately from the crosslinking step.

In some aspects, a step subsequent to crosslinking comprises providing particles of the crosslinked GAG molecule, having an average size in the range of 0.01-5 mm, preferably 0.1-0.8 mm.

In some aspects, the particles are between 20 to 800 μm in size. In some aspects, the particles are between about 100 to about 500 μm in size. In some aspect, this size may be length, diameter, or width. In general, this refers to diameter.

In some aspects, the particles are between 20 to 800 µm, between 20 to 700 µm, between 20 to 600 µm, between 20 to 500 µm, between 20 to 400 between 20 to 300 between 20 to 200 between 100 to 800 µm, between 100 to 700 µm, or between 100 to 300 µm in size.

In some aspects, the coupling agent is a peptide coupling reagent. In some aspects the coupling reagent is selected from 4-(4,6-dimethoxy-1,3,5-triazin-2-yl)-4-methylmorpholinium chloride (DMTMM) and 2-chloro-4,6-dimethoxy-1,3,5-triazine (CDMT). A preferred triazine-based peptide coupling reagent is DMTMM. Other preferred peptide coupling reagent are carbodiimide coupling reagents, preferably N-(3-dimethylanninopropyl)-N'-ethylcarbodiinnide (EDC) combined with N-hydroxysuccinimide (NHS).

In some aspects, crosslinking of the activated GAG molecules occurs via their carboxyl groups using a crosslinker. In some aspects, the crosslinker is a di- or multinucleophile functional crosslinker comprising a spacer group selected from the group consisting of di-, tri-, tetra-, and oligosaccharides. In some aspects, the crosslinker connects the GAG chains to each other via carboxyl groups on the GAG backbone. In some aspects, the spacer group may be a hyaluronic acid tetrasaccharide, hyaluronic acid hexasaccharide, trehalose, lactose, maltose, sucrose, cellobiose or raffinose residue. By the term "residue" is meant here that the structure of the compound is similar but not identical to the patent compounds hyaluronic acid tetrasaccharide, hyaluronic acid hexasaccharide, trehalose, lactose, maltose, sucrose, cellobiose or raffinose respectively. The structure of the residue may differ from the structure of the parent compound in that it has been provided with two or more nucleofile functional groups and optionally covalently linked via said nucleophile functional groups carboxyl groups on the GAG backbone.

According to a related aspect, the present invention also provides use of the hydrogel product as a medicament, such as in the treatment of soft tissue disorders. There is provided a method of treating a patient suffering from a soft tissue disorder by administering to the patient a therapeutically effective amount of the hydrogel product. There is also provided a method of providing corrective or aesthetic treatment to a patient by administering to the patient a therapeutically effective amount of the hydrogel product.

In some aspects, the hydrogel contains mostly liquid by weight and can contain 90-99.9%, water, but it behaves like a solid due to a three-dimensional crosslinked GAG molecule network within the liquid. Due to its significant liquid content, the hydrogel is structurally flexible and similar to natural tissue, which makes it very useful as a scaffold in tissue engineering and for tissue augmentation. It is also useful for treatment of soft tissue disorder and for corrective or esthetic treatment. In some aspects, the hydrogel is used as an injectable formulation.

The methods disclosed herein are methods of using the injectable compositions for reparative or plastic surgery, esthetic dermatology, facial contouring, body contouring, and gingival augmentation. In some aspects, the compositions are freeze-dried or lyophilized. In some aspects, the compositions comprise a hydrogel comprising an aqueous solution.

In some aspects, a crosslinked glycosaminoglycan product, such as hyaluronic acid product, is produced from high molecular weight (HMW) glycosaminoglycan using amide crosslinking.

In some aspects, a crosslinked hyaluronic acid product from HMW hyaluronic acid using DATH/DMTMM chemistry is formulated to create a suitable GAG concentration for use ($C_{final}$ of 10-45 mg/mL). In some aspects, the GAG is a hyaluronic acid. In some aspects, the suitable GAG concentration is for dermatological use, dental use, medical use, or reconstructive surgical use.

In some aspects, the suitable GAG concentration is 10 to 50 mg/mL, 10 to 45 mg/mL, 10 to 40 mg/mL, 10 to 35 mg/mL, 10 to 30 mg/mL, 10 to 25 mg/mL, 10 to 20 mg/mL, 10 to 15 mg/mL, 15 to 40 mg/mL, 15 to 40 mg/mL, 15 to 35 mg/mL, 15 to 30 mg/mL, 15 to 25 mg/mL, 15 to 20 mg/mL, 20 to 50 mg/mL, 20 to 45 mg/mL, 20 to 40 mg/mL, 20 to 35 mg/mL, 20 to 30 mg/mL, 20 to 25 mg/mL, 25 to 50 mg/mL, 25 to 45 mg/mL, 25 to 40 mg/mL, 25 to 35 mg/mL, 25 to 30 mg/mL, 30 to 50 mg/mL, 30 to 45 mg/mL, 30 to 40 mg/mL, 30 to 35 mg/mL, 35 to 50 mg/mL, 35 to 45 mg/mL, 35 to 40 mg/mL, 40 to 50 mg/mL, or 40 to 45 mg/mL.

In some aspects, the suitable GAG concentration is about 10 to about 50 mg/mL, about 10 to about 45 mg/mL, about 10 to about 40 mg/mL, about 10 to about 35 mg/mL, about 10 to about 30 mg/mL, about 10 to about 25 mg/mL, about 10 to about 20 mg/mL, about 10 to about 15 mg/mL, about 15 to about 40 mg/mL, about 15 to about 40 mg/mL, about 15 to about 35 mg/mL, about 15 to about 30 mg/mL, about 15 to about 25 mg/mL, about 15 to about 20 mg/mL, about 20 to about 50 mg/mL, about 20 to about 45 mg/mL, about 20 to about 40 mg/mL, about 20 to about 35 mg/mL, about 20 to about 30 mg/mL, about 20 to about 25 mg/mL, about 25 to about 50 mg/mL, about 25 to about 45 mg/mL, about 25 to about 40 mg/mL, about 25 to about 35 mg/mL, about 25 to about 30 mg/mL, about 30 to about 50 mg/mL, about 30 to about 45 mg/mL, about 30 to about 40 mg/mL, about 30 to about 35 mg/mL, about 35 to about 50 mg/mL, about 35 to about 45 mg/mL, about 35 to about 40 mg/mL, about 40 to about 50 mg/mL, or about 40 to about 45 mg/mL.

In some aspects, hyaluronic acid encompasses all variants and combinations of variants of hyaluronic acid, hyaluronate, or hyaluonan—of various chain lengths and charge states, as well as various chemical modifications, including crosslinking.

In some aspects, hyaluronic acid encompasses the various hyaluronate salts of hyaluronic acid with various counter ions, such as sodium hyaluronate. In some aspects, various modifications of hyaluronic acid are also encompassed by recitation of hyaluronic acid, such as oxidation, e.g. oxidation of —CH$_2$OH groups to —CHO and/or —COOH; periodate oxidation of vicinal hydroxyl groups, which may be followed by reduction, e.g. reduction of —CHO to —CH$_2$OH or coupling with amines to form imines followed by reduction to secondary amines; sulphation; deamidation, which may be followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. In some aspects, hyaluronic acid may be further modified by isourea, hydrazide, bromocyan, monoepoxide, and monosulfone couplings.

In some aspects, hyaluronic acid may be obtained from various sources of animal and non-animal origin. In some aspects, sources of non-animal origin include yeast or bacteria. In some aspects, the molecular weight of a single hyaluronic acid molecule is typically in the range of 0.1 to 10 mDa, but other molecular weights are possible.

In some aspects, the present disclosure is drawn to at least the partial deacetylation of a biopolymer/hydrogel comprising acetyl groups, comprising: a) providing a biopolymer comprising acetyl groups; b) reacting the biopolymer comprising acetyl groups with hydroxylamine or a salt thereof at a temperature of 100° C. or less for 2 to 200 hours to form an at least partially deacetylated biopolymer, and c) recovering the at least partially deacetylated biopolymer. In some aspects, the hydrogel is prepared from HMW GAGs through the methods described herein.

In some aspects, the present disclosure is drawn to a method of preparing a hydrogel product comprising crosslinked GAGs, the method comprising: a) providing a GAG crosslinked by amide bonds, wherein the crosslinked GAGs comprise residual amine groups, and b) acylating residual amine groups of the crosslinked GAGS provided in a) to form acylated crosslinked GAGs. In some aspects, the hydrogel is prepared from HMW GAGs through the methods described herein.

In some aspects, the present disclosure is drawn to a method of preparing a hydrogel product comprising crosslinked GAGs, the method comprising: a) providing a GAG crosslinked by aminde bonds, wherein the crosslinked GAGs comprise ester crosslinks formed as byproducts during the amide crosslinking; and b) subjecting the crosslinked GAGs to alkaline treatment to hydrolyze ester crosslinks formed as byproducts during the amide crosslinking. In some aspects, the hydrogel is prepared from HMW GAGs through the methods described herein.

When producing hydrogels from a high molecular weight (HMW) glycosaminoglycan, such as hyaluronic acid, with the DATH/DMTMM system using low DATH loading, a suitable gel for filler composition is initially formed, but the hydrogel may hydrolyze upon storage or during exposure to degrading conditions (e.g. heat sterilization, accelerated stability studies). This indicates that a larger number of crosslinks is needed to keep the gel intact and protect it against hydrolysis. However, increasing the amount of DATH/DMTMM—to increase the number of crosslinks in the gel—may lead to gels with high $C_{min}$ that are phase separated at suitable GAG concentrations. In other words, when producing gels from HMW GAGs with enough crosslinks to make them stable during autoclaving it isn't possible to dilute the gels to 20 mg/ml (10-45 mg/ml) without obtaining phase separation. This will in turn add complexity to the process for e.g. filling the gel in syringes. In some aspects, the hydrogel is homogeneous. A homogeneous product is not phase separated. In some aspects, the hydrogel is formulated to a suitable concentration for dermatological use (such as 10-45 mg/mL), but retains the capacity to swell in the presence of excess saline.

In some aspects, the method of producing a hydrogel does not result in phase separation of the hydrogel. In some aspects, a hydrogel produced or derived from the methods disclosed herein is not phase separated. In some aspects, the method of diluting a hydrogel after heat sterilization does not result in phase separation of the hydrogel.

In some aspects, the hydrogel is diluted in a PBS buffer. In some aspects, the hydrogel is diluted in a 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM phosphate buffer. In some aspects, the hydrogel is diluted in about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM phosphate buffer. In some aspects, the hydrogel is diluted to between 1 mM to 20 mM, 1 mM to 15 mM, 1 mM to 10 mM, 1 mM to 5 mM, 5 mM to 20 mM, 5 mM to 15 mM, 5 mM to 10 mM, 10 mM to 20 mM, 10 mM to 15 mM, or 15 mM to 20 mM phosphate buffer. In some aspects, the hydrogel is diluted to between about 1 mM to about 20 mM, about 1 mM to about 15 mM, about 1 mM to about 10 mM, about 1 mM to about 5 mM, about 5 mM to about 20 mM, about 5 mM to about 15 mM, about 5 mM to about 10 mM, about 10 mM to about 20 mM, about 10 mM to about 15 mM, or about 15 mM to about 20 mM phosphate buffer.

In some aspects, the hydrogel is diluted in a solution at a pH of about 6.0, about 6.2, about 6.4, about 6.6, about 6.8, about 7.0, about 7.2, about 7.4, about 7.6, about 7.8, or about 8.0. In some aspects, the hydrogel is diluted in a solution at a pH of 6.0, 6.2, 6.4, 6.6, 6.8, 7.0, 7.2, 7.4, 7.6, 7.8, or 8.0. In some aspects, the hydrogel is diluted in a solution at a pH of between 6.0 to 8.0, between 6.0 to 7.0, between 7.0 and 8.0, between 6 and 7.5, between 7.0 and 7.5, or between 6.5 and 7.5.

In some aspects, the HA concentration of the crosslinking reaction is about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20%. In some aspects, the HA concentration of the crosslinking reaction is 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% 11%, 12%, 13%, 14%, 15%, 16%, 17%, 18%, 19%, or 20%. In some aspects, the HA concentration of the crosslinking reaction is between 1% to 3%, 2% to 5%, 3% to 5%, 4% to 5%, 2% to 3%, 2% to 4%, 3% to 5%, 3% to 4%, 1% to 20%, 1% to 15%, 1% to 10%, 1% to 5%, 1% to 2%, 2% to 5%, 2% to 10%, 2% to 15%, 2% to 20%, 5% to 20%, 5% to 15%, 5% to 10%, 10% to 20%, 10% to 15%, or 15% to 20%.

In some aspects, the HA concentration of the crosslinking reaction is not greater than 10%. In some aspects, the HA concentration of the crosslinking reaction is not greater than 9%. In some aspects, the HA concentration of the crosslinking reaction is not greater than 8%. In some aspects, the HA concentration of the crosslinking reaction is not greater than 7%. In some aspects, the HA concentration of the crosslinking reaction is not greater than 6%. In some aspects, the HA concentration of the crosslinking reaction is not greater than 5%. In some aspects, the HA concentration of the crosslinking reaction is not greater than 4%. In some aspects, the HA concentration of the crosslinking reaction is not greater than 3%.

In some aspects, the mol-% of DATH in the crosslinking reaction is 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2%. In some aspects, the mol-% of DATH in the crosslinking reaction is about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%. In some aspects, the mol-% of DATH in the crosslinking reaction is 0.1% to 2%, 0.1% to 1.5%, 0.1% to 1%, 0.1% to 0.5%, 0.2% to 1%, 0.2% to 0.5%, 0.2% to 0.3%, 0.5% to 1%, 0.5% to 1.5%, 0.5% to 2%, 1% to 2%, or 1% to 1.5%.

In some aspects, the GAG has a molecular weight of above 700 kDa, 800 kDa, 900 kDa, 1000 kDa, 1100 kDa, 1200 kDa, 1300 kDa, 1400 kDa, 1500 kDa, 1600 kDa, 1700 kDa, 1800 kDa, 1900 kDa, 2000 kDa, 2500 kDa, 3000 kDa, 3500 kDa, 4000 kDa, 4500 kDa, 5000 kDa, 5500 kDa, 6000 kDa, 6500 kDa, 7000 kDa, 7500 kDa, 8000 kDa, 8500 kDa, 9000 kDa, 9500 kDa, or 10000 kDa.

In some aspects, the GAG has a molecular weight of above about 700 kDa, about 800 kDa, about 900 kDa, about 1000 kDa, about 1100 kDa, about 1200 kDa, about 1300 kDa, about 1400 kDa, about 1500 kDa, about 1600 kDa, about 1700 kDa, about 1800 kDa, about 1900 kDa, about 2000 kDa, about 2500 kDa, about 3000 kDa, about 3500 kDa, about 4000 kDa, about 4500 kDa, about 5000 kDa, about 5500 kDa, about 6000 kDa, about 6500 kDa, about 7000 kDa, about 7500 kDa, about 8000 kDa, about 8500 kDa, about 9000 kDa, about 9500 kDa, or about 10000 kDa.

In some aspects, the thermostability (NormGelC or GelC) of the hydrogel is at least 80% after 24 hours. In some aspects, the thermostability (NormGelC or GelC) of the hydrogel is at least 80% after 48 hours. In some aspects, the thermostability (NormGelC or GelC) of the hydrogel is at least 80% after 24 hours at about 90° C. In some aspects, the thermostability (NormGelC or GelC) of the hydrogel is at least 80% after 24 or 48 hours at a temperature of at least 70° C. In some aspects, the thermostability (NormGelC or GelC) of the hydrogel is at least 80% after 24 or 48 hours at a temperature of at least 90° C.

In some aspects, the thermostability (NormGelC or GelC) of the hydrogel is at least 70%, 75%, 80%, 85%, 90%, or 95% after 24 hours or 48 hours. In some aspects, the thermostability (NormGelC or GelC) of the hydrogel is at least 70%, 75%, 80%, 85%, 90%, or 95% after 24 hours or 48 hours at a temperature of at least 70° C. or at least 90° C.

In some aspects, the thermostability (NormGelC or GelC) of the hydrogel is at least about 70%, about 75%, about 80%, about 85%, about 90%, or about 95% after 24 hours or 48 hours. In some aspects, the thermostability (NormGelC or GelC) of the hydrogel is at least 70%, 75%, 80%, 85%, 90%, or 95% after 24 hours or 48 hours at a temperature of at least 70° C. or at least 90° C.

In some aspects, the thermostability (NormGelC or GelC) of the hydrogel decreases by less than 5%, 10%, 15%, 20%, 25%, or 30% after 24 hours or 48 hours at a temperature of at least 70° C. or at least 90° C. In some aspects, the thermostability (NormGelC or GelC) of the hydrogel decreases by less than about 5%, about 10%, about 15%, about 20%, about 25%, or 30% after 24 hours or 48 hours at a temperature of at least 70° C. or at least 90° C.

In some aspects, the temperature at which the thermostability is determined is at least 70° C., 72° C., 74° C., 76° C., 78° C., 80° C., 82° C., 84° C., 86° C., 88° C., 90° C., 92° C., 94° C., 96° C., 98° C., 100° C., 102° C., 104° C., 106° C., 108° C., or 110° C. In some aspects, the temperature at which the thermostability is determined is at least about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., about 100° C., about 102° C., about 104° C., about 106° C., about 108° C., or about 110° C.

In some aspects, the period of time post-manufacture at which the thermostability is determined is at least 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, 72 hours, 74 hours, 76 hours, 78 hours, or 80 hours. In some aspects, the period of time post-manufacture at which the thermostability is determined is at least about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, about 50 hours, about 52 hours, about 54 hours, about 56 hours, about 58 hours, about 60 hours, about 62 hours, about 64 hours, about 66 hours, about 68 hours, about 70 hours, about 72 hours, about 74 hours, about 76 hours, about 78 hours, or about 80 hours.

In some aspects the composition is bioresorbable. In some aspects, the hydrogel is bioresorbable. In some aspects, the composition is bioresorbed within a period of about 1 year to about 3 years. In some aspects, the composition is bioresorbed within a period of 1 year to 3 years. In some aspects, the hydrogel is bioresorbed within a period of about 1 year to about 3 years. In some aspects, the hydrogel is bioresorbed within a period of 1 year to 3 years.

In some aspects, the composition further comprises a local anesthetic. In some aspects, the composition comprises at least one local anesthetic. In some aspects the local anesthetic is an amide-type local anesthetic. In some aspects, the local anesthetic is an ester-type local anesthetic.

In some aspects, the local anesthetic is selected from the group consisting of: bupivacaine, butanilicaine, carticaine, cinchocaine (dibucaine), clibucaine, ethyl parapiperidino-acetylaminobenzoate, etidocaine, lignocaine (lidocaine), mepivacaine, oxethazaine, prilocaine, ropivacaine, toly-caine, trimecaine, vadocaine, articaine, levobupivacaine, amylocaine, cocaine, propanocaine, clormecaine, cyclom-ethycaine, proxymetacaine, amethocaine (tetracaine), ben-zocaine, butacaine, butoxycaine, butyl aminobenzoate, chlo-roprocaine, dimethocaine (larocaine), oxybuprocaine, piperocaine, parethoxycaine, procaine (novocaine), propoxycaine, and tricaine; or a combination thereof.

In some aspects, the concentration of local anesthetic in the composition is between 1 to 5 mg/mL. In some aspects, the concentration of local anesthetic in the composition is between about 1 to about 5 mg/mL. In some aspects, the concentration of local anesthetic in the composition is between 2 to 4 mg/mL. In some aspects, the concentration of local anesthetic in the composition is between about 2 to about 4 mg/mL. In some aspects, the concentration of local anesthetic in the composition is 0.5 mg/mL, 1 mg/mL, 1.5 mg/mL, 2 mg/mL, 2.5 mg/mL, 3 mg/mL, 3.5 mg/mL, 4 mg/mL, 4.5 mg/mL, or 5 mg/mL. In some aspects, the concentration of local anesthetic in the composition is about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, or about 5 mg/mL.

In some aspects, the composition is injectable. In some aspects, the injectable composition is an injectable implant. In some aspects, the disclosure is drawn to an injectable implant comprising any one of the compositions disclosed herein. In some aspects, the injectable implant is for sub-dermal, intradermal, subcutaneous, intramuscular, submus-cular, intragingival injection.

In some aspects, the disclosure is drawn to a pre-filled syringe comprising any one of the compositions disclosed herein. In some aspects, the disclosure is drawn to a pre-filled vial comprising any one of the compositions disclosed herein.

In some aspects, a kit comprises a pre-filled syringe comprising any one of the compositions disclosed herein. In some aspects, a kit comprises a pre-filled vial comprising any one of the compositions disclosed herein, a syringe, and one or more hypodermic needles. In some cases the kit comprises an antimicrobial composition for administering to the site of injection.

In some aspects, kits for use in practicing the methods described herein are contemplated. In some aspects, kits comprise all solutions, buffers, compounds, vessels, and/or instructions sufficient for performing the methods described herein.

In some aspects, the composition further comprises sodium chloride. In some aspects, the composition exhibits a sodium chloride concentration of 0.9% w/v. In some aspects, the composition further comprises a phosphate buffer. In some aspects, the composition further comprises a pharmaceutically acceptable carrier. In some aspects the composition further comprises sodium chloride, a phosphate buffer, and a pharmaceutically acceptable carrier.

In some aspects, the composition comprises one or more density enhancing agents. In some aspects, the density enhancing agents may be selected from sorbitol, mannitol, and fructose.

In some aspects, the composition comprises a buffering agent. A buffering agent is a chemical compound that is or compounds that are added to a solution to allow that solution to resist changes in pH as a result of either dilution or small additions of acids or bases. Effective buffer systems employ solutions which contain large and approximately equal concentrations of a conjugate acid-base pair (or buffering agents). A buffering agent employed herein may be any such chemical compound(s) which is pharmaceutically acceptable, including but not limited to salts (conjugates acids and/or bases) of phosphates and citrates. In some aspects, the buffering agent comprises phosphate buffered saline (PBS) or an alternative phosphate buffer.

In some aspects, the composition is aseptic. In some aspects, the composition is sterile. In some aspects, the composition is sterilized via filtration sterilization, heat sterilization, or irradiation sterilization. In some aspects, components of the composition are sterilized prior to mixing or forming the whole composition, thus resulting in a composition that comprises two or more components that were sterilized prior to forming the composition.

In some aspects, the GAG does not have a molecular weight of less than 1.5 MDa. In some aspects, the GAG does not have a molecular weight of less than 1.4 MDa. In some aspects, the GAG does not have a molecular weight of less than 1.3 MDa. In some aspects, the GAG does not have a molecular weight of less than 1.2 MDa. In some aspects, the GAG does not have a molecular weight of less than 1.1 MDa. In some aspects, the GAG does not have a molecular weight of less than 1.0 MDa. In some aspects, the GAG does not have a molecular weight of less than 0.9 MDa. In some aspects, the GAG does not have a molecular weight of less than 0.8 MDa. In some aspects, the GAG does not have a molecular weight of less than 0.7 MDa.

In some aspects, the hydrogel is not subjected to a post-crosslinking degradation of the glycosaminoglycan. In some aspects, the hydrogel is subject to ambient degradation post-crosslinking; however, the hydrogel does not exhibit a $C_{min}$ value below that of $C_{final}/2$. In some aspects, the hydrogel exhibits a $C_{min}$ value greater than $C_{final}/2$ of the hydrogel.

Other aspects and preferred embodiments of the present invention will be evident from the following detailed disclosure of the invention and the appended claims.

II. Methods of Using the Hydrogels

In some aspects, the present disclosure comprises methods of performing reparative or esthetic dermatologic treatment. In some aspects, the reparative or esthetic dermatologic treatment comprises injecting a subject with a composition disclosed herein. In some aspects, the injection is a subdermal, intradermal, subcutaneous, intramuscular, submuscular, or intragingival injection.

In some aspects, methods of the present disclosure are drawn to intragingival injection to fill the gums as a result of receding gums. In some aspects, methods are drawn to injection of the composition in one or more tissues of the oral cavity.

In some aspects, the injection is for dermal filling, body contouring, facial contouring, and gingival filling.

In some aspects, the injection of a composition disclosed herein is for dermal filling. In some aspects, methods of dermal filling include injection of the composition to fill skin cracks. In some aspects, methods of dermal filling include injection of the composition to fill fine lines in the face, neck, hands, feet, knees, and elbows. In some aspects, methods of dermal filling include injection of the composition to fill fine wrinkles in the face, neck, hands, feet, knees, and elbows. In some aspects, methods of dermal filling include injection of the composition to fill fine lines in the face, neck, hands, feet, knees, and elbows.

In some aspects, methods of dermal filling include injection of the composition to fill scars. In some aspects, methods of dermal filling include injection of the composition to fill depressed scars. In some aspects, methods of dermal filling include injection of the composition to fill hypertrophic scars. In some aspects, methods of dermal filling include injection of the composition to fill keloid scars.

In some aspects, methods of dermal filling include injection of the composition to restore and/or correct for signs of facial fat loss (lipoatrophy) in people with human immunodeficiency virus (HIV).

In some aspects, methods of dermal filling include injection of the composition to the backs of hands or the top of feet.

In some aspects, methods of dermal filling include injection of the composition to strengthen weakened vocal cords.

In some aspects, methods of dermal filling include injection of the composition to restore lost volume to a portion of the body as a result of age, illness, or injury.

In some aspects, methods of facial contouring include injection of the composition to the face to modify the facial contour. In some aspects, methods of facial contouring include injection of the composition to the lips to augment the size and/or shape of the lips.

In some aspects, methods of facial contouring include injection of the composition to the face to increase facial symmetry. In some aspects, methods of facial contouring include injection of the composition to change the shape of the face to an oval shape, round shape, square shape, triangle shape, inverted triangle shape, rectangular shape, or oblong shape. In some aspects, methods of facial contouring include injection of the composition to increase the total width of the face. In some aspects, methods of facial contouring include injection of the composition to increase the total length of the face.

In some aspects, methods of facial contouring include injection of the composition to the face to increase the forehead and/or cheekbone width. In some aspects, methods of facial contouring include injection of the composition to the face to increase the length of the jawline.

In some aspects, methods of facial contouring include injection of the composition to the face to change the size and/or shape of the chin. In some aspects, methods of facial contouring include injection of the composition to the face to change the size and/or shape of the forehead. In some aspects, methods of facial contouring include injection of the composition to the face to change the size and/or shape of the cheeks. In some aspects, methods of facial contouring include injection of the composition to the face to change the size and/or shape of the brow.

In some aspects, methods of facial contouring include injection of the composition to the face to modify the appearance associated with retrognathia. In some aspects, methods of facial contouring include injection of the composition to the face to modify the appearance associated with prognathism.

In some aspects, methods of body contouring include injection of the composition to the body to modify the size and shape of various aspects of the body. In some aspects, methods of body contouring include injection of the composition to the body to modify the size and shape of aspects of the body to increase symmetry.

In some aspects, methods of body contouring include injection of the composition to the body to modify the size and shape of the breasts, buttocks, sacrum, groin, hips, abdomen, thorax, feet, legs, knees, popliteus, thighs, arms, hands, elbows, and/or antecubitis, In some aspects, methods of body contouring include injection of the composition to the body to fill a concave deformity. In some aspects, the concave deformity is a result of age, illness, injury, or predisposition. In some aspects, methods of body contouring include injection of the composition to the body to decrease the appearance of cellulite.

EXAMPLES

Example 1

High Molecular Weight Hydrogel Production

Example 1 provides the general process for making high molecular weight GAG hydrogels described herein.

Hyaluronic acid (HA) and solutions of diamino trehalose (DATH) and 4-(4,6-dimethoxy-1,3,5-triazin-2-yl)-4-methyl-morpholinium chloride (DMTMM) are mixed to crosslink. After the crosslinking process, the gel is divided and diluted to a set concentration. Thereafter, the gel is heated to approximately 70° C. for approximately 24 hours. The gel then undergoes particle size reduction (PSR) and precipitation, and is then washed and dried to a powder. The gel powder is then mixed into a suitable buffer and the gel swells; the gel is then autoclaved.

TABLE 1

Hydrogel compositions corresponding to FIG. 1.

| | Reaction Conditions | | | Gel Properties | | | |
|---|---|---|---|---|---|---|---|
| Sample | DATH/HA (mol %) | [HA] (%) | Mw (MDa) | SwF (mL/g) | GelC (%) | CrR | $C_{final}$ (mg/g) |
| 1-1 | 0.9 | 3.5 | 1.0 | 5.2 | 87 | ND | 20 |
| 1-2 | 0.9 | 4 | 1.0 | 4.2 | 87 | ND | 20 |
| 1-3 | 0.9 | 3.5 | 2.1 | 4 | 96 | ND | 20 |
| 1-4 | 0.9 | 4 | 2.1 | 3.2 | 98 | 0.31 | 19 |

ND = Not determined

The Gel Content was analyzed under heat degradation conditions at 90° C. and evaluated over the course of just over 70 hours (FIG. 1). The gel content values are normalized for ease of comparison, which is depicted as "NormGelC (%)" in the y-axis of FIG. 1. The data indicates that the high molecular weight HA provides gels that maintain a higher degree of gel content under heat degradation conditions as compared to the gels made from the lower molecular weight HA.

Example 2

Preparing and Evaluating High Molecular Weight (HMW) and Low Molecular Weight (LMW) Hyaluronic Acid (HA) Hydrogels

General Procedure for Crosslinking BMW and LMW HA

Stock solutions of each of DMTMM and the DATH crosslinker were freshly prepared in water. A reaction solution was prepared by adding desired volumes of the DMTMM (mol % DATH×8.5) and DATH (see Table 1) stock solutions, respectively, to water. The reaction solution was mixed and directly added to pre-weighted HA (0.4 MDa or 2.1 MDa) in a reaction vessel. The mixture was extensively mixed for 3 min and incubated. After 24±2 h, the obtained material was pressed through a 1 mm steel mesh. The material was homogenized for 24±2 h at 70° C. before the gel was subjected to particle size reduction (PSR) using a 3×315 μm filter and then precipitated by adding EtOH. The obtained powder was dried under vacuum overnight and reconstituted in 7 mM phosphate, 0.7% NaCl and 3 mg/g Lido-HCl at neutral pH. The gel was filled in syringes and subsequently autoclaved.

TABLE 2

Reactions conditions and obtained gel properties.

| | Reaction Conditions | | | Gel Properties | | | |
|---|---|---|---|---|---|---|---|
| Sample | DATH/HA (mol %) | [HA] (%) | Mw (MDa) | SwF (mL/g) | GelC (%) | CrR | $C_{final}$ (mg/g) |
| 2-1 | 1.5 | 2 | 0.4 | 10.6 | 44 | 0.17 | 20 |
| 2-2 | 1.5 | 2 | 2.1 | 6.2 | 91 | 0.20 | 20 |
| 2-3 | 0.3 | 10 | 0.4 | 5.4 | 74 | 0.55 | 40 |
| 2-4 | 0.3 | 10 | 2.1 | 2.7 | 95 | 0.50 | 40 |
| 2-5 | 0.5 | 6 | 0.4 | 5.9 | 75 | 0.38 | 25 |
| 2-6 | 0.5 | 6 | 2.1 | 2.9 | 94 | 0.37 | 25 |
| 2-7 | 0.9 | 4 | 0.4 | 4.9 | 83 | 0.32 | 20 |
| 2-8 | 0.9 | 4 | 2.1 | 3.2 | 98 | 0.28 | 20 |

The gels were incubated in sealed glass vials at 90° C. in a water bath for 24 hours or 48 hours. At the given time, the samples were cooled to room temperature and the gels were analyzed. See FIGS. 2-4

Figure 2:
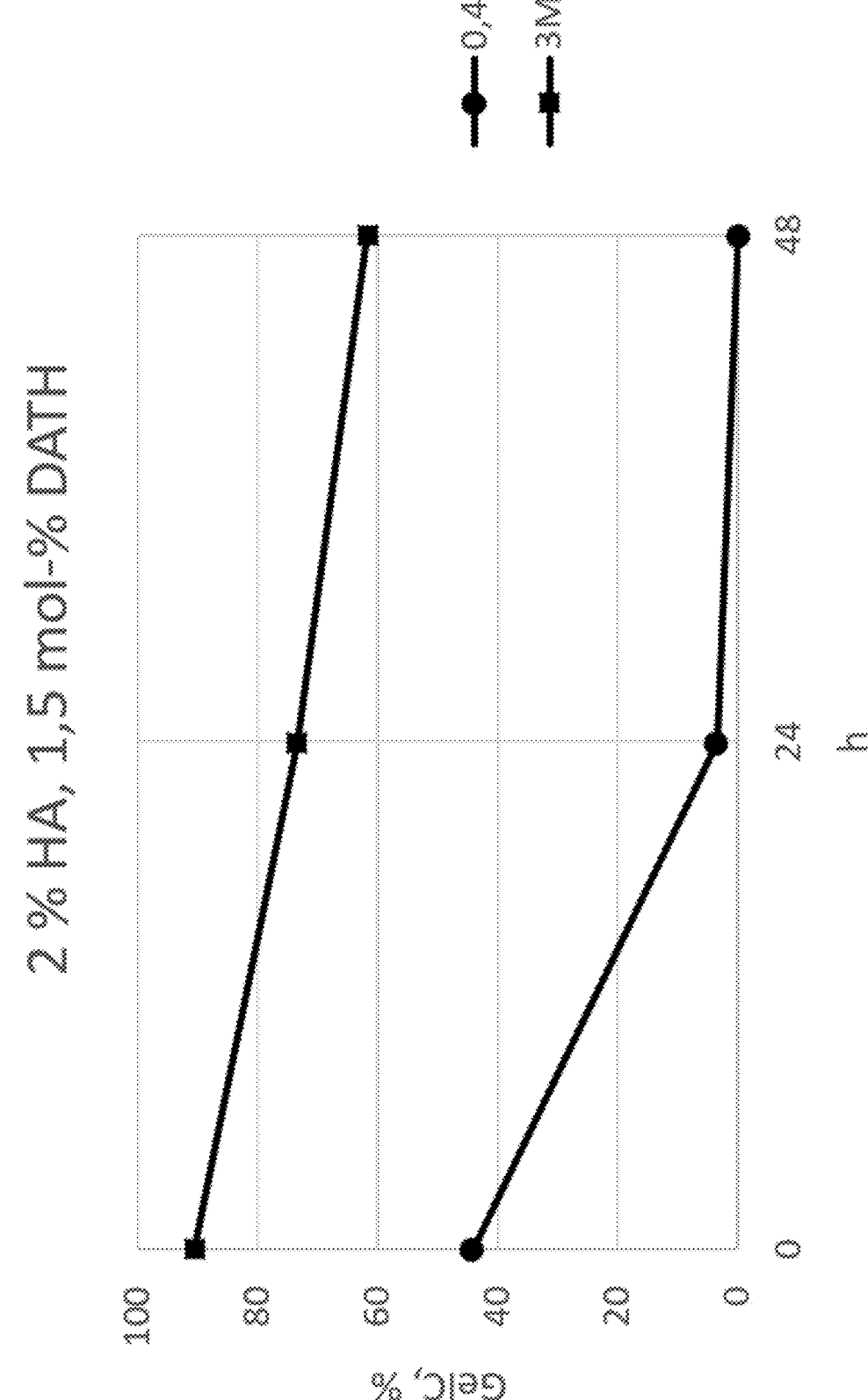
FIG. 2 depicts the gel content (GelC %) corresponding to samples 1 and 2 in Table 2 after the gels were incubated at 90° C. for 24 or 48 hours.
Figure 3:
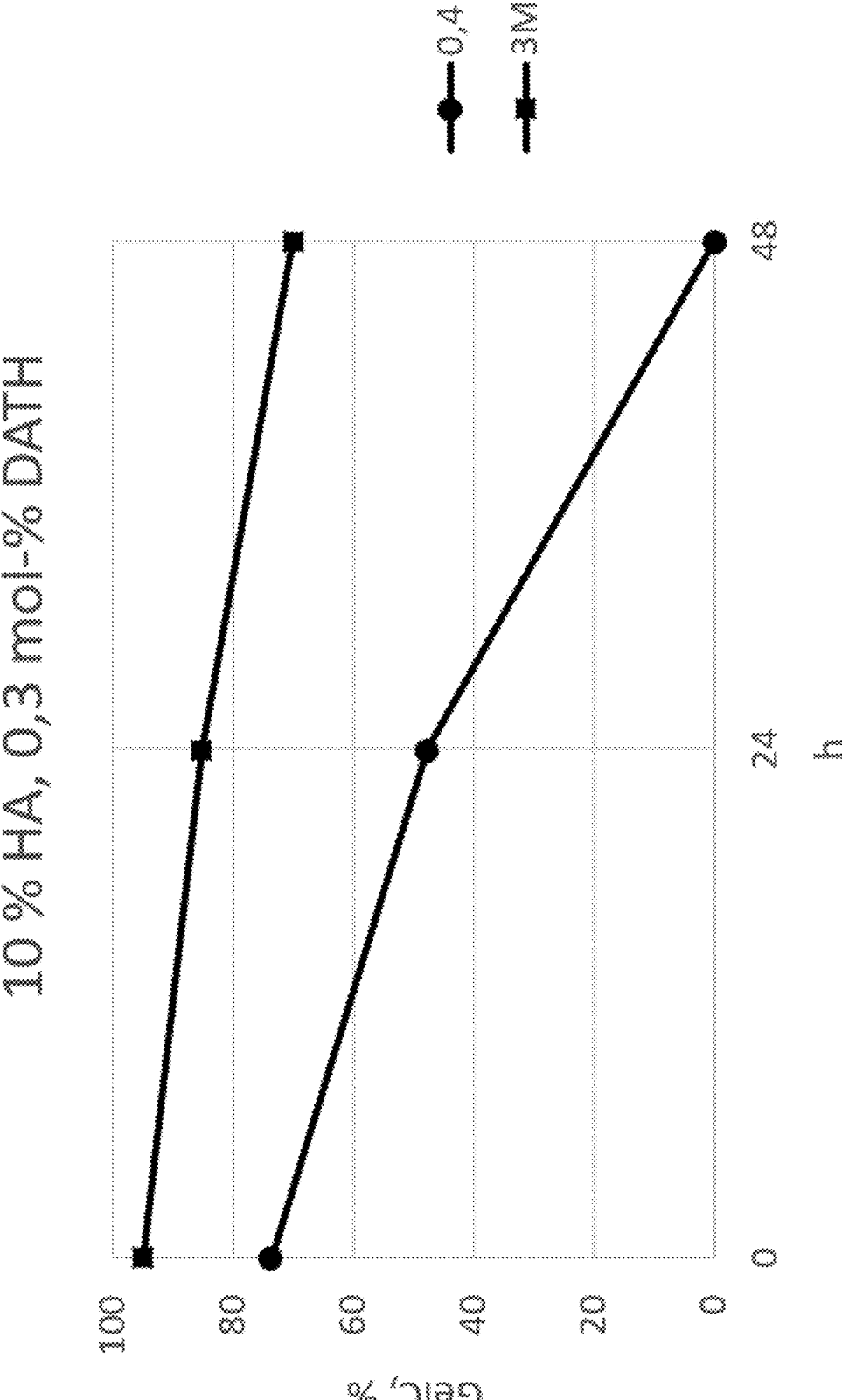
FIG. 3 depicts the gel content (GelC %) corresponding to samples 3 and 4 in Table 2 after the gels were incubated at 90° C. for 24 or 48 hours.
Figure 4:
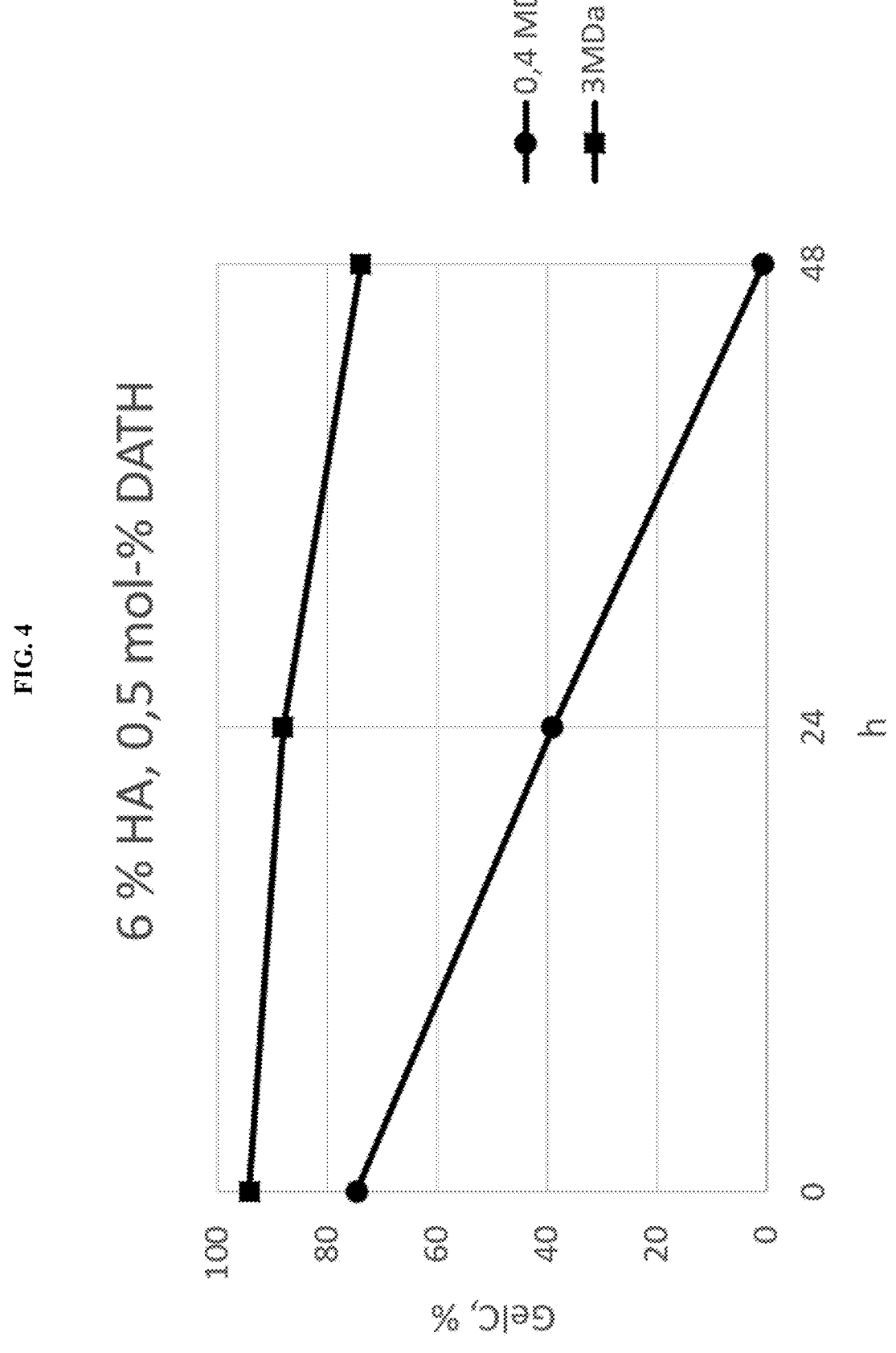
FIG. 4 depicts the gel content (GelC %) corresponding to samples 5 and 6 in Table 2 after the gels were incubated at 90° C. for 24 or 48 hours.
Figure 5:
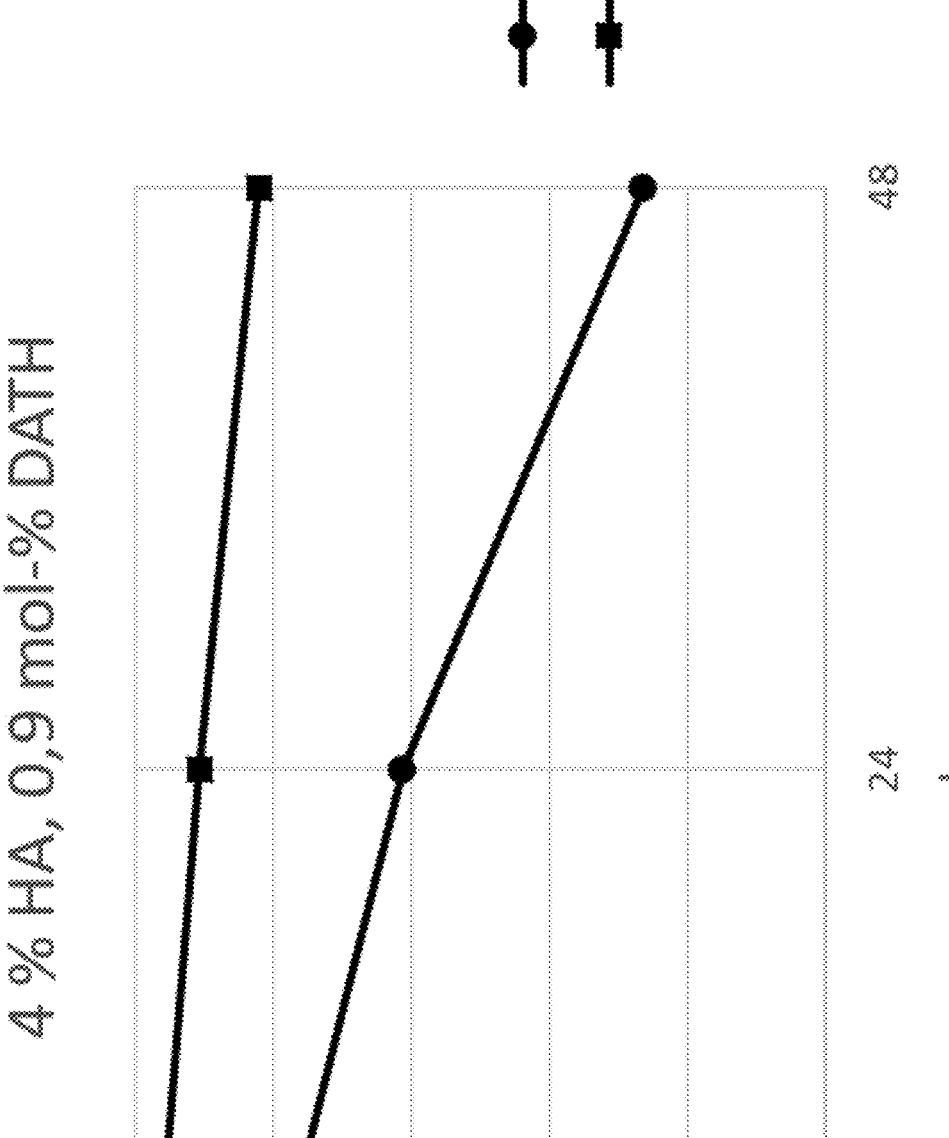
FIG. 5 depicts the gel content (GelC %) corresponding to samples 7 and 8 in Table 2 after the gels were incubated at 90° C. for 24 or 48 hours.

FIG. 2 depicts the gel content (GelC %) corresponding to samples 2-1 and 2-2 in Table 2. FIG. 3 depicts the gel content (GelC %) corresponding to samples 2-3 and 2-4 in Table 2. FIG. 4 depicts the gel content (GelC %) corresponding to samples 2-5 and 2-6 in Table 2. FIG. 5 depicts the gel content (GelC %) corresponding to samples 2-7 and 2-8 in Table 2.

General Procedure for Determining the $MW_{app}$ in HMW Gels

Pre-weighted HA (2.1 MDa) was mixed with water in a reaction vessel. The mixture was extensively mixed for 3 min and incubated at ambient temperature. After 24 hours, the solution was diluted with water, NaCl(s) was added (final concentration 0.9%), and the obtained material was incubated at 70° C. After incubation for 24 hours, the solution was filled in syringes. Syringes for sample 2-10 was subsequently autoclaved while the syringes for sample 2-9 were not. The Mw of the solutions were determined by SEC-MALLS.

TABLE 3

Reaction conditions and obtained gel properties.

| | Reaction Conditions | | | | | |
|---|---|---|---|---|---|---|
| | DATH/ HA | | | Properties | | |
| Sample | (mol-%) | [HA] (%) | Mw (MDa) | Mw$_{app}$ (MDa) | Polydisp. | Comment |
| 2-9 | 2 | 4 | 2.1 | 2.2 | 2.2 | Not autoclaved |
| 2-10 | 0 | 4 | 2.1 | 1.4 | 2.1 | Autoclaved |

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein. The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

In addition, where features or aspects of the disclosure are described in terms of Markush groups, those skilled in the art will recognize that the disclosure is also thereby described in terms of any individual member or subgroup of members of the Markush group.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed:

1. A hydrogel product comprising a hyaluronic acid hydrogel crosslinked by amide bonds, obtained by a method comprising:
   crosslinking a hyaluronic acid (HA) having a molecular weight of 2.1 to 10 MDa with a crosslinker, to obtain the hyaluronic acid hydrogel crosslinked by amide bonds, wherein:
   the crosslinker is a di- or multinucleophile functional crosslinker comprising a spacer group selected from the group consisting of di-, tri-, tetra-, and oligosaccharides;
   a concentration of the HA is between 2% to 10% (w/w); and
   a molar ratio of the crosslinker to the HA is less than or equal to 2 mol % per HA disaccharide.

2. The hydrogel product according to claim 1, wherein the spacer group is trehalose.

3. The hydrogel product according to claim 1, wherein the di- or multinucleophile functional crosslinker is diaminotrehalose (DATH).

4. The hydrogel product according to claim 1, wherein the HA has a molecular weight of 2.1-3.5 MDa.

5. The hydrogel product according to claim 1, wherein:
   the HA has a molecular weight of 2.1-3.5 MDa;
   the crosslinker is diaminotrehalose (DATH); and
   during the crosslinking, the concentration of HA is between 3-5% (w/w) and the molar ratio of DATH to HA is between 0.9-1.1 mol % per HA disaccharide.

6. The hydrogel product according to claim 1, wherein the hydrogel product is essentially free of synthetic non-carbohydrate structures or linkers.

7. The hydrogel product according to claim 1, wherein the crosslinked HA molecules have an apparent molecular weight (Mwapp) above 1.0 MDa.

8. The hydrogel product according to claim 1, wherein the crosslinked HA molecules have an apparent molecular weight (Mwapp) of 2.1 MDa or above.

9. The hydrogel product according to claim 1, wherein the hydrogel product has a HA concentration of 10-45 mg/mL.

10. The hydrogel product according to claim 1, wherein the crosslinking comprises:
   (1) providing a solution of the HA molecules;
   (2) activating carboxyl groups on the HA molecules with a coupling agent to form activated HA molecules;
   (3) crosslinking the activated HA molecules via their activated carboxyl groups using a di- or multinucleophile functional crosslinker to obtain a HA hydrogel crosslinked by amide bonds.

11. The hydrogel product according to claim 1, wherein the concentration of the HA is between 3-5% (w/w) during the crosslinking.

12. The hydrogel product according to claim 1, wherein the molar ratio of crosslinker to HA is between 0.9-1.1 mol % per HA disaccharide during the crosslinking.

13. The hydrogel product according to claim 1, further comprising a local anesthetic.

14. The hydrogel product according to claim 13, wherein the local anesthetic comprises lidocaine.

15. A syringe comprising the hydrogel product according to claim 1.

16. A method of performing a reparative or esthetic dermatologic treatment, the method comprising:

injecting a subject with the hydrogel product of claim 1.

17. The method of claim 16, wherein the injecting is performed as a subdermal, intradermal, subcutaneous, intramuscular, submuscular, or intragingival injection.

18. The method of claim 16, wherein the reparative or esthetic dermatologic treatment comprises dermal filling.

19. The method of claim 18, wherein the injection is administered to fill lines, fine lines, wrinkles, or skin cracks.

20. The method of claim 19, wherein the lines, fine lines, wrinkles, or skin cracks are located on the face, neck, hands, feet, knees, or elbows.

\* \* \* \* \*